United States Patent [19]
Plasek et al.

[11] 3,951,977

[45] Apr. 20, 1976

[54] 4-HIGH MOLECULAR WEIGHT ALKYL-SUBSTITUTED CARBOPHENOXY PHTHALIC ACID-CONTAINING COMPOUNDS

[75] Inventors: Edmund J. Plasek, Chicago; Imre Puskas, Lisle, both of Ill.

[73] Assignee: Standard Oil Company, Chicago, Ill.

[22] Filed: Sept. 16, 1970

[21] Appl. No.: 72,831

[52] U.S. Cl. ................ 260/268 BC; 260/326 A; 260/340.2; 252/392; 252/51.5 A; 252/56 R
[51] Int. Cl.$^2$ ............. C07D 295/10; C07D 209/48
[58] Field of Search ...... 260/326 N, 326 A, 268 BC

[56] References Cited
UNITED STATES PATENTS
3,461,136  8/1969  Pruckmayr et al. ................ 260/326

*Primary Examiner*—Joseph A. Narcavage
*Attorney, Agent, or Firm*—Fred R. Ahlers; Arthur G. Gilkes; William T. McClain

[57] ABSTRACT

Title compounds are 4-[alkyl-substituted carbophenoxy] phthalic anhydride, acid, mono- and diesters, mono- and diamines and imides. These compounds are obtained by reaction of water, alcohols, amino-alcohols and nitrogen-containing compounds having at least one HN< group with 4-[alkyl-substituted carbophenoxy] phthalic anhydride which can be obtained by the reaction of a 4-acid halide of trimellitic anhydride with an alkyl-substituted phenol wherein the alkyl-substituent has thirty or more carbon atoms. The title compounds are soluble in mineral oil and function therein as anti-wear, anti-rust or dispersant-detergent addition agents.

7 Claims, No Drawings

4-HIGH MOLECULAR WEIGHT ALKYL-SUBSTITUTED CARBOPHENOXY PHTHALIC ACID-CONTAINING COMPOUNDS

BACKGROUND OF THE INVENTION

Trimellitic acid (1,2,4-benzene tricarboxylic acid) although known for some time, has only become commercially available in recent years in the form of its intra-molecular anhydride, trimellitic anhydride, which also may be named 4-carboxyphthalic anhydride. Interest in this trifunctional acid and its simple or monomolecular anhydride has been mainly in the preparation of simple triesters, for example trimethyl, triethyl, triesters from primary $C_6$ and $C_8$ oxo-alcohols and trialkyl esters among related simple esters; poly-(amide-imides) resin mainly from diamines which are aromatic in nature; and polyesters related to alkyd resins wherein alkyd forming diols and triols are used with modification by oil-type fatty acids, mono- and di-basic acids to obtain oil or water base surface coating compositions.

Little attention, other than to simple esters as synthetic oils, has been publicized for the potential use of trimellitic acid or its simple anhydride as a building block for the preparation of derivatives soluble in mineral oil, such as the mineral lubricant oils, which would provide addition agents therefor to improve the lubricant oil in service use. It may well be that potential lubricant oil addition agents have been prepared from trimellitic acid or its simple anhydride and have been found to be unsuccessful for the intended additive purpose and, like other unsuccessful research, gone unpublished. Such lack of success may well have come about by the unusual reactivity of the simple anhydride of trimellitic acid. Each of the three carboxyl groups of trimellitic acid have substantially the same reactivity. But the 4-carboxyl group of the simple anhydride is somewhat less reactive than the carboxyl equivalents of the anhydride ring.

That different reactivity makes difficult the introduction of a variety of groups by way of varying carboxyl group modification to introduce two or more new and different functional groups. Also the trifunctionality of trimellitic acid and its simple anhydride is available to cause cross-linking which, although leading to high molecular weight end products with new and varied functional groups, also leads to gel or resin formation not generally desirable for lubricant oil addition agents.

We have discovered a novel class of compounds which are derivatives of trimellitic acid and are soluble in mineral oil. Some members of this class are detergent-dispersant addition agents and hence are useful in the formation of crankcase lubricant oils. Other members of this class, while not meeting present day requirements for detergency-dispersancy function in crankcase lubricant oils, are oil soluble and provide anti-wear or anti-rust or synthetic oil addition agents useful in the formulation of crankcase lubricant oils, or greases or other lubricants where those additive functions are needed.

SUMMARY OF THE INVENTION

Our novel class of trimellitic acid derivatives all contain the 4-[alkyl-substituted carbophenoxy] group, wherein the alkyl-substituent contains 30 or more carbon atoms. Said novel class of derivatives are all derived from a 4-acid halide, preferbly 4-acid chloride, of the simple trimellitic acid anhydride. The simplest member of said 4-[alkyl-substituted carbophenoxy]-containing derivatives of trimellitic acid is the anhydride which can be illustrated structurally as follows:

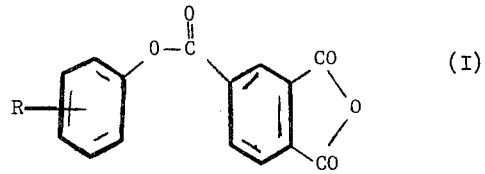

wherein R is the alkyl-substituent having 30 or more carbon atoms. Said R group (alkyl-substituent) can be on a ring carbon ortho or para with respect to the ring carbon attached to the oxygen atom. The species of compounds of formula I can be named as 4-alkylphenyl ester of trimellitic acid anhydride. But this would not well serve as a class name for other members of the class derived from reactions involving the difunctional anhydride ring. Hence the class family name for compounds of formula (I) and derivatives thereof will be hereafter based on 4-(alkyl-substituted carbophenoxy) phthalic anhydride.

Other members of the novel class of 4-[alkyl-substituted carbophenoxy] phthalic anhydride include the phthalic acid analog which has the same structure of formula (I) except the anhydride ring is opened (e.g., with 1 mole of water) and is replaced by two vicinal carboxyl groups; simple mono- and diesters derived from monohydroxy alcohols, R'—OH wherein R' is an alkyl group of 1 to 30 carbon atoms; mono- and di-hydroxyalkyl esters derived from di- and trihydroxy alcohols; mono- and di-ether esters derived from alkoxy alkanols and hydroxy alkoxy alkanols; mono- and diamides derived from nitrogen-containing compounds having at least one HN< group; and imides derived from nitrogen containing compounds having at least one $H_2N$— group, i.e., amines.

Members of the simplest form of the novel inventive compounds, i.e., compounds having formula (I) are readily prepared by reaction of an alkyl-substituted phenol whose alkyl-substituent has 30 or more carbon atoms with the 4-acid halide of trimellitic anhydride in equi-molecular proportions under conditions which remove the by-product hydrogen halide formed. Said hydrohalide is of no further use in this reaction, is not needed for the preparation of other members of the novel inventive class of compounds and its presence is undesirable for the lubricant formulating use for which said novel class of compounds can be used to advantage. Since by-product hydrogen chloride is more readily removed than the other hydrogen halides, preference is for 4-acid chloride of trimellitic acid as the reactant with the alkyl-substituted phenol. Hereinafter said 4-acid chloride of trimellitic anhydride is, for convenience, referred to as "TMAC."

The reaction of TMAC with the alkyl-substituted phenol (alkyl group of 30 or more carbon atoms) is not a novel reaction. The reactions involved in the preparation of the diacid analog, the ester, hydroxy ester, amide and imide derivatives of compounds having the structure of formula (I) also are not novel reactions because they are of the same types known from the preparations of analogous derivatives of phthalic anhydride. In those preparative methods where water is a by-product, it is common expedient to conduct at least a portion of the reaction under conditions which remove by-product water. Also the use of catalysis where advantageous to produce analogous phthalic anhydride derivatives will, in general, be found to be advantageous in the preparation of like derivatives of compounds having the structure of formula (I).

EMBODIMENTS OF THE INVENTION

A. Alkyl-Substituent in Formula (I)

Suitable alkyl-substituents are those, as before mentioned, having 30 or more carbon atoms. The lower limit of 30 carbon atoms is essential to insure oil-solubility at least in the concentration range of 0.01 to 10.0 weight percent which is the range ordinarily used for addition agents used with mineral oils of the lubricating oil types. The upper carbon atom limit of the alkyl-substituent does not appear to be critical for oil-solubility but rather is, as a practical matter, imposed only by the size availability of alkyl-substituted phenols or the size availability of alkylating agents (alcohols or mono-olefins) reacted with phenol in the preparation of the alkyl-substituted phenol. The size of the alkyl-substituent upward from 30 carbon atoms does not change the reactivity of the alkylphenol, does not enter into any of the reactions and thus the alkyl-substituent can be any size above 30 carbon atoms. The practical size upper limit of the alkyl-substituent is 214 carbon atoms and thus a range of 30–214 carbon atoms which, when polyolefin derived as hereafter described, is represented by such $C_{30}$–$C_{214}$ alkyl-substituents as having the number average molecular weight ($\overline{M}_n$) of 420–3000.

At present the availability of reactants to supply the alkyl-substituent on the phenol ring provides a practical limitation on the size of the alkyl-substituent of about 3000 number average molecular weight ($\overline{M}n$) because these alkylating agents are primarily mono-olefinic polybutenes. Such polybutenes are polymers from the Friedel-Crafts catalyzed polymerization of isobutylene and mixtures of the isomeric butenes: butene-1, butene-2 and isobutylene. Usually $AlCl_3$ is the catalyst for the preparation of such polybutenes and the resulting product has some, about 20 weight percent saturated polymer insofar as reactivity is concerned and about 80 weight percent mono-olefinic reacting polymer having a single terminal double bond. The saturated polymer will be recognized as occurring from hydrogen transfer typically caused by $AlCl_3$. Polypropenes obtained by $AlCl_3$ catalyzed polymerization of propene likewise are similar mixtures of saturated and unsaturated polymers but the upper limit in $\overline{M}n$ for polypropenes is about 1200 $\overline{M}n$. The polybutenes and polypropenes are both suitable reactants for preparation of the alkyl-substituted, respectively polybutyl and polypropyl, phenols. Said 3000 $\overline{M}n$ represent a number average ($\overline{M}n$) carbon content of about 214.

Other suitable alkyl-substituted phenols whose alkyl groups have from 30 and upward carbon atoms are those obtained from the alkylation of phenol with natural or synthetic alcohols, or olefins derived from petroleum wax hydrocarbons and other high molecular weight petroleum fractions.

The alkyl-substituted phenol supplying the alkyl-substituent in formula (I) above thus has for present practical purposes 30 to 214 carbon atoms and preferably is a polybutyl-substituted phenol wherein the polybutyl-substituent has 30 to 214 total carbon atoms.

B. The Alcohol Reactants

Ester derivatives of Formula I compounds are obtained by reacting Formula I type compounds with a compound containing at least one —OH group such as mono-, di-, tri-, tetra-, and hexa-hydric alcohols; aldoses; mono-, di- and poly-alkoxy alcohols; hydroxyalkoxy alcohols; tri-(hydroxyalkyl)amines; and hydroxy aromatic compounds in the respective reactant molar ratio of 1.0:1.0–2.0. Specific —OH group containing reactants include the $C_1$–$C_{12}$ monohydric alcohols: methanol, ethanol, n-propanol, isopropanol, n-butanol, isobutyl alcohol, sec.-butyl alcohol, tert.-butyl alcohol, n-amyl alcohol, isoamyl alcohol, 2-ethyl-1-propanol, sec.-amyl alcohol, diethycarbinol, tert.-amyl alcohol, tert.-butyl carbinol, methyl-isopropyl carbinol, n-hexyl alcohol, oxo-hexyl alcohols, oxo-hexyl alcohols, n-heptyl alcohol, oxo-heptyl alcohols, n-octyl alcohol, 2-ethyl hexanol, oxo-octyl alcohols, n-nonyl alcohol, oxo-nonyl alcohols, n-decyl alcohol, oxo-decyl alcohols, n-dodecyl alcohol, oxodecyl alcohols, cyclopentanol, cyclohexanol, methylcyclohexanols, benzyl alcohol and phenylethanol; dihydric alcohols: ethylene glycol, 1,2-propylene glycol, trimethylene glycol, tetramethylene glycol, pentamethylene glycol, hexamethylene glycol, heptamethylene glycol, octamethylene glycol, nonamethylene glycol, decamethylene glycol, dodecamethylene glycol and their equivalent alkylene oxides

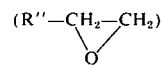

wherein R'' is hydrogen or alkyl having 1 to 10 carbon atoms; the tri-, tetra-, hepta- and hexa-hydric alcohols glycerol, 1,2,3-trihydroxybutane, erythritol, dulcitol, d-mannitol, d-sorbitol; the aldoses: d-glyceric aldehyde, threose, erythrose, lyxose, xylose, arabinose, ribose, talose, galactose, idose, gulose, fructose, mannose, glucose, altrose and allose; the mono-, di- and poly-alcohols: methoxyethanol, ethoxyethanol, propoxyethanol, butoxyethanol, amoxyethanol, hexoxyethanol, octoxyethanol, decoxyethanol, dodecoxyethanol, methoxypropanol, 2-methoxy-2-methyl ethanol, ethoxypropanol, 2-ethoxy-2-methylethanol, 2-propoxypropanol, 2-propoxy-2-methylethanol, isopropoxy-2-methyl-ethanol, butoxy-2-methylethanol, isobutoxy-2-methyl ethanol, methoxyethoxyethanol, 2-methoxyethoxy-2-methylethanol, ethoxyethoxyethanol, propoxyethoxyethanol, propoxy-2-methylethoxy-2-methylethanol, methoxy-ethoxyethoxyethanol, ethoxyethoxyethoxyethanol, propoxyethoxyethoxyethanol, butoxyethoxyethoxyethanol, and methoxypropoxypropoxyethoxyethanol; hydroxyethoxyethanol, hydroxypropoxypropanol, di(2-hydroxy-2-methyl)-ethyl ether, hydroxyethoxypropanol, 2-hydroxyethoxy-2-methylethanol and like ethers of the other foregoing dihydric alcohols; tri(hydroxymethyl)amine, tri(hydroxyethyl)amine, tri(hydroxypropyl)amine, tri(2-hydroxy-2-methylethyl)amine and like tri(hydroxyalkyl)amine derivatives of the other foregoing dihydric alcohols and ammonia condensed in the respective reactant molar ratio of 3.0:1.0; and the hydroxyaromatic compounds: phenol, cresols, ethylphenols, xylenols, thymol, carvacol, naphthols, pyrocatechol, resorcinol, hydroquinone, pyrogallol, hydroxyhydroquinone, phloroglucinol, hydroxy diphenyl, benzylphenol, phenethylphenol and tolylnaphthol among others.

C. The Amine Reactants

The amines contemplated herein are those which contain an amino group characterized by the presence of at least one active hydrogen atom. Such amines may contain only primary amino groups, only secondary amino groups, or both primary and secondary groups. Typical amines are the polyalkylpolyamines, ethylenediamine, propylenediamine, polyalkene polyamines (e.g., diethylene triamine, triethylene tetramine); the aromatic amines o-, m- and p-phenylene diamine, diamino naphthalenes; the acid substituted polyalkylpolyamines, N-acetyl tetraethylenepentamine, and the corresponding formyl-, propionyl-, butyroyl-, and the like N-substituted compounds; and the corresponding cyclized compounds formed therefrom, such as the N-alkyl amines of imidazolidine and pyrimidine. Secondary heterocyclic amines which are suitable are those characterized by attachment of a hydrogen atom to a nitrogen atom in the heterocyclic group. Representative of the amines contemplated herein are morpholine, thiomorpholine, pyrrole, pyrroline, pyrrolidine, indole, pyrazole, pyrazoline, pyrazolidine, imidazole, imidazoline, imidazolidine, piperidine, phenoxazine, phenthiazine and their substituted analogs. Substituent groups attached to the carbon atoms of these amines are typified by alkyl aryl, alkaryl, aralkyl, cycloalkyl, and amino compounds referred to above.

Suitable alkylene polyamine reactants include ethylendiamine, diethylene triamine, triethylene tetramine, tetraethylene pentamine, pentaethylene hexamine, hexaethylene heptamine, heptaethylene octamine, octaethylene nonamine, nonaethylene decamine and decaethylene undecamine and mixture of such amines having nitrogen contents corresponding to the alkylene polyamines, in the formula $H_2N-(A-N-H-)_nH$, mentioned before, A is divalent ethylene and $n$ is 1 to 10 of the foregoing formula. Corresponding propylene polyamines such as propylene diamine and di-, tri-, tetra-, penta-propylene tri-, tetra-, penta- and hexa-amines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloro alkanes having 2 to 6 carbon atoms and the chlorines on different carbons are suitable alkylene polyamine reactants.

Also suitable are condensation products of urea or thiourea and the alkylene polyamines wherein for each X moles of urea or thiourea 2X moles of alkylene polyamine are used. Such a condensation product from two moles of alkylene polyamine and one mole of urea has the formula:

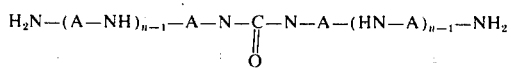

Also suitable are polyalkylpolyamines having the formula:

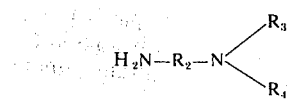

wherein $R_2$ is a divalent alkylene radical containing 1 to 8 carbon atoms and $R_3$ and $R_4$ are each alkyl radicals having 1 to 6 carbon atoms. Such polyalkylpolyamines are $C_1$ to $C_6$ dialkyl N-substituted derivatives of the alkylene polyamines mentioned above. Illustrative $R_3$ and $R_4$ substituents include N',N'-dimethyl-, N',N',-diethyl, N',N'-di-n-propyl, N',N'-di-isopropyl, N',N'-di-n-butyl, N',N'-diisobutyl, N',N'-di-tert.-butyl, N',-N'-di-n-amyl, N',N'-di-isoamyl, N',N'-di-tert.-amyl, N',N'-di-n-hexyl, N',N'-di-n-octyl, N',N'-di-(2-ethylhexyl) N',N'-di-(2-methylheptyl), N',N'-dinonyl, N',-N'-didecyl and N',N'-didodecyl among other substituted 1,2-ethanediamine, 1,2-propanediamine, 1,3-propane diamine, 1,3-hexane diamine, 1,6-hexamine diamine, 1,3-pentane diamine, 1,3-butane diamine, 1,4-butane diamine and other like $C_1$–$C_6$ alkane diamines.

Also suitable as amine reactants are the hydroxyalkyl substituted amines which have at least one reactive hydrogen on a nitrogen. Such hydroxy alkyl-substituted amines can be derivatives of ammonia primary amines, diamono alkanes and alkylene polyamines derived therefrom by reaction with epichlorohydrin or its homologs or analogs. Illustrative of such hydroxyalkyl-substituted amines are mono- and di-hydroxyethyl amine; mono- and di-hydroxypropyl amine; mono- and di-2-hydroxypropylamine; mono-hydroxyethyl methylamine; mono-hydroxy ethylamine; mono-hydroxyethyl hexylamine; mono-hydroxy-octylamine; mono-2-hydroxypropyl methylamine; mono-2-hydroxypropyl hexylamine; mono-, di- and tri-hydroyethyl ethylene diamine; mono- to tetrahydroxyethyl ethylene diamine; mono- through tri-hydroxyethyl hexane diamine; mono- through tri-2-hydroxypropyl ethylene diamine; hydroxyethyl cyclohexylamine; mono- through tri-hydroxyethyl phenylene diamine, mono- through tri-2-hydroxypropyl phenylene diamine; mono- through trihydroxyethyl cyclohexane diamine; mono- through tri-2-hydroxypropyl cyclohexane diamine; and mono- through tri-hydroxyethyl bis-aminopropyl piperazine among other like hydroxyalkyl-substituted amines.

ILLUSTRATIVE EMBODIMENTS

The following examples are presented to illustrate the preparation of compounds of this invention and are not intended to be a limitation of the preparative method or the products prepared.

EXAMPLE 1

Polybutylphenol of 1600 $\overline{M}_n$ (polybutyl group has Mn of about 1500 or 107 number average carbon atoms) is reacted with trimellitic anhydride acid chloride (phthalic anhydride 4-acid chloride) to prepare a member of the class of compounds of Formula I wherein R is said $C_{107}$ polybutyl group.

To a solution in polybutene ($\overline{M}_n$ 1500) containing 46.5 weight percent or 0.648 mole of said 1600 $\overline{M}_n$ polybutylphenol there is added 530 grams of SAE 5W oil. The resulting solution is stirred and heated to 300°F. and then 136 grams (0.648 mole) of molten trimellitic anhydride acid chloride (210 MW) are added. The resulting mixture is stirred and heated to 440°F. and held between 440° and 460°F. for 3 hours while injecting nitrogen gas into the liquid reaction mixture to assist removal of by-product HCl.

The resulting product is a solution containing 40 weight percent of 4-[polybutylcarbophenoxy] phthalic anhydride wherein the polybutyl group contains 107 number average carbon atoms ($\overline{M}_n$ of 1500) and has a viscosity of 860 SSU at 210°F.

EXAMPLE 2

To 1900 grams of the product solution of Example 1, which contains 0.43 mole of 4-[polybutylcarbophenoxy] phthalic anhydride, there are added 53 grams of SAE 5W oil and 40 (0.43 mole) grams glycerol. Said mixture is stirred and heated to a temperature maintained within the range of 300° to 320°F. for 3 hours while injecting nitrogen gas into the liquid to assist removal of by-product water. The resulting solution is filtered and yields a dark clear liquid containing 40 weight percent of an isomeric mixture of mono- and di-2-methylolethyl 4-[polybutylcarbophenoxy] phthalates which have the formula:

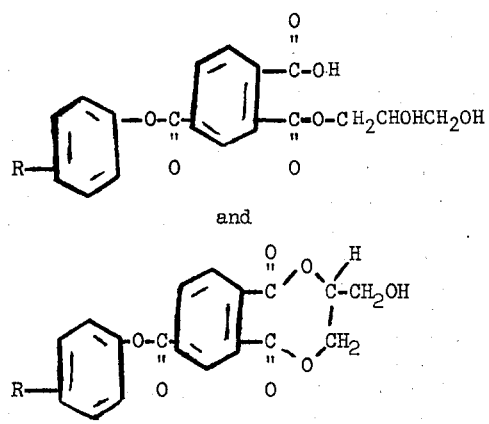

wherein R is polybutyl of 1500 $\overline{M}_n$.

EXAMPLE 3

The preparative method of Example 2 is repeated except 20 grams (0.215 mole) of glycerol is used in place of 40 grams of glycerol. The resulting filtrate contains 40 weight percent of an isomeric mixture of mono-dihydroxypropyl 4-[polybutylcarbophenoxy] acid phthalate.

EXAMPLE 4

The preparative method of Example 2 is repeated except 0.43 mole of sorbitol is used in place of 0.43 mole of glycerol. The liquid filtrate contains 40 weight percent of an isomeric mixture of tetrahydroxyhexyl 4-[polybutylcarbophenoxy] phthalate.

EXAMPLE 5

The preparative method of Example 2 is repeated except 0.645 mole of sorbitol is used in place of 0.43 mole of glycerol and the reaction is conducted for 16 hours. The liquid filtrate contains 40 weight percent mixture of sorbitolyl 4-[polybutylcarbophenoxy] phthalate.

EXAMPLE 6

The preparative method of Example 2 is repeated except 0.482 mole sorbitol is used in place of 0.43 mole of glycerol and the reaction is conducted for 16 hours. The liquid filtrate contains 40 weight percent mixture of sorbitolyl 4-[polybutylcarbophenoxy] phthalate.

EXAMPLE 7

The preparative method of Example 2 is repeated except 0.86 mole of sorbitol is used in place of 0.43 mole of glycerol and the reaction is conducted for 16 hours. The liquid filtrate contains 42 weight percent mixture of sorbitolyl 4-[polybutylcarbophenoxy] phthalates.

EXAMPLE 8

The preparative method of Example 2 is repeated except 0.43 mole dextrose is used in place of 0.4 mole of glycerol. The liquid filtrate contains 40 weight percent mixture of dextrosyl 4-[polybutylcarbophenoxy] phthalates.

EXAMPLE 9

The preparative method of Example 2 is repeated except 0.54 mole of tetra-hydroxyethyl methane is employed in place of 0.43 mole of glycerol. The liquid filtrate contains 40 weight percent mixture of 3-(trihydroxyethyl) propyl 4-[polybutylcarbophenoxy] phthalates.

EXAMPLE 10

The preparative method of Example 2 is repeated except 0.43 mole of glycol is employed in place of 0.43 mole of glycerol. The liquid filtrate contains 40 weight percent mixture of mono-2-hydroxyethyl 4-[polybutylcarbophenoxy] phthalates.

EXAMPLE 11

The preparative method of Example 2 is repeated except 0.43 mole of tri-(2-hydroxyethyl) amine is used in place of 0.43 mole of glycerol. The liquid filtrate contains 40 weight percent of N,N'-di-2-hydroxyethylaminoethyl 4-[polybutylcarbophenoxy] phthalate.

EXAMPLE 12

The preparative method of Example 2 is repeated except 0.86 mole of methanol is employed in place of 0.43 mole of glycerol and pressure is employed to maintain methanol in the liquid phase. The liquid filtrate contains 40 weight percent dimethyl 4-[polybutylcarbophenoxy] phthalate.

EXAMPLE 13

The preparative method of Example 2 is repeated except 0.43 mole of ethanol is employed in place of 0.43 mole of glycerol and pressure is employed to maintain ethanol in the liquid phase. The liquid filtrate contains 40 weight percent mono-ethyl 4-[polybutylcarbophenoxy] phthalate.

EXAMPLE 14

The preparative method of Example 2 is repeated except 0.86 mole of cyclohexanol is used in place of 0.43 mole of glycerol. The liquid filtrate contains 40 weight percent dicyclohexyl 4-[polybutylcarbophenoxy] phthalate.

EXAMPLE 15

The preparative method of Example 2 is repeated except 0.86 mole of 2-ethylhexanol is used in place of 0.43 mole glycerol. The liquid filtrate contains 40 weight percent di(2-ethylhexyl)-4-[polybutylcarbophenoxy] phthalate.

Ester products analogous to the foregoing illustrative esters can be prepared from 4-[polypropylcarbophenoxy] phthalic anhydride wherein the polypropyl group contains 30 to 57 number average carbon atoms; i.e., polypropyl group as a $\overline{M}_n$ in the range of 420 to 800. Likewise esters homologous to the foregoing ester products can be prepared from 4-[polybutylcarbophenoxy] phthalic anhydride wherein the polybutyl group contains 28 to 214 number average carbon atoms, i.e., the polybutyl group has a $\overline{M}_n$ in the range of 400 to 3000.

EXAMPLE 16

There is prepared in the following manner 4-[polypropylcarbophenoxy] phthalic anhydride wherein R of Formula I is polypropyl of 800 $\overline{M}_n$, i.e., the polypropyl group contains 57 number average carbon atoms. Equimolecular amounts of molten trimellitic anhydride acid chloride and polypropylphenol (854 $\overline{M}_n$) wherein the polypropyl group has 54 number average carbon atoms, dissolved in xylene are combined under pressure, stirred and heated to 400°F. Pressure is maintained to keep a liquid phase of xylene. After six hours reaction, xylene is distilled off leaving said 4-[polypropylcarbophenoxy] phthalic anhydride as a residue.

The preparative method of Example 16 can be used to prepare the 4-[polybutylcarbophenoxy] phthalic anhydride of Example 1 when that product is not desired as an oil solution thereof. The 4-[alkylcarbophenoxy] phthalic anhydride compounds of Formula I (alkyl has 30–3000 carbon atoms) so prepared can be reacted with the hydroxy compounds to form ester products in the presence of solvents other than hydrocarbon oils, for example n-hexane, benzene, toluene and xylene. Likewise, the illustrative derivatives hereinafter described can also be prepared in solvents other than hydrocarbon oils. However, since compounds of Formula I and derivatives thereof are mainly useful as lubricant addition products, it is most convenient to prepare them as solutions in hydrocarbon solvents of the lubricating oil class.

EXAMPLE 17

A solution containing 40 weight percent of the 4-[polybutylcarbophenoxy] phthalic anhydride (polybutyl group of 1500 $\overline{M}_n$) described as product of Example 1 to provide 0.25 mole thereof is stirred and heated to 200°F. Thereafter ammonia in excess of 0.5 mole is injected into the hot liquid. Then the stirred solution is heated to 300°F. and ammonium gas injection is replaced by nitrogen gas injection to assist the removal of excess ammonia and by-product water. The hot liquid is filtered. The filtrate contains 40 weight percent 4-[polybutylcarbophenoxy] phthalamide.

EXAMPLE 18

A quantity of 40 weight percent solution containing 0.25 mole of the 4-[polybutylcarbophenoxy] phthalic anhydride (polybutyl group of 1500 $\overline{M}_n$) described in Example 1 is stirred and heated to 150°F. Then 0.23 mole of polyoxypropylene diamine (190 M.W.) is added, the stirred mixture is heated to 250°F. and nitrogen gas is injected to assist the removal of by-product water. The liquid filtrate contains 40 weight percent of 4-[polybutylcarbophenoxy] phthalamide of polyoxypropylene diamine.

EXAMPLE 19

A quantity of 40 weight percent solution containing 0.20 mole of the 4-[polybutylcarbophenoxy] phthalic anhydride (polybutyl group of 1500 $\overline{M}_n$) described in Example 1 is stirred and heated to 150°F. Then 0.10 mole of N,N'-bis-aminopropyl piperazine is added to the stirred solution. The resulting stirred mixture is gradually heated to 250°F. and nitrogen gas is injected to assist the removal of by-product water. The liquid filtrate contains 40 weight percent di[polybutylcarbophenoxy] phthalimide of N,N'-bis-aminopropyl piperazine and has a nitrogen content of 0.55 weight percent.

EXAMPLE 20

The preparative method of Example 19 is repeated except 0.142 mole of bis-aminopropyl piperazine is used in place of 0.1 mole thereof. The liquid filtrate contains 40 weight percent of a reaction product containing mainly 1:1 mono-imide analog of product of Example 19.

EXAMPLE 21

The preparative method of Example 19 is repeated except 0.1 mole tetraethylene pentamine is used in place of 0.1 mole bis-aminopropyl piperazine. The liquid filtrate contains 40 weight percent di-4-[polybutylcarbophenoxy] phthalimide of tetraethylene pentamine.

EXAMPLE 22

The preparative method of Example 21 is repeated except the tetraethylene pentamine is increased to 0.184 mole. The liquid filtrate contains 40 weight percent of an amide reaction product which is a mixture of tetraethylene pentamine amides and acid amides of 4-[polybutylcarbophenoxy] phthalic acid.

EXAMPLE 23

The preparative method of Example 19 is repeated except 0.2 mole of N',N'-dimethylethylenediamine is used in place of 0.1 mole of the bis-aminopropyl piperazine. The liquid filtrate contains 4-[polybutylcarbophenoxy] phthalimide of said dimethylethylenediamine.

EXAMPLE 24

A solution of 0.1 mole of 4-[polypropylcarbophenoxy] phthalic anhydride, wherein the polypropyl-substituent has a 425 $\overline{M}_n$ or 30 carbon atoms number average carbon atoms, in xylene is prepared. This solution is stirred and heated to 140°F. and thereafter 0.1 mole of N',N'-dihydroxyethyl ethylene diamine is added to the stirred solution. The resulting stirred solution is heated to xylene reflux temperature for about 2 hours and then xylene is removed by distillation. The residue is 4-[polypropylcarbophenoxy] phthalimide of N',N'-dihydroxyethyl ethylenediamine which is soluble in lubricating oils and aliphatic hydrocarbons.

EXAMPLE 25

A solution of 0.2 mole of 4-[polypropylcarbophenoxy] phthalic anhydride, wherein the polypropyl-substituent has an 800 $\overline{M}_n$ or 57 number average carbon atoms, in toluene. This solution is stirred and heated to 160°F. and then 0.2 mole of aniline is added. The resulting stirred mixture is heated to 220°F. for 2 hours and then toluene is distilled therefrom. The residue is N-phenyl 4-[polypropylcarbophenoxy] phthalimide which is soluble in lubricating oil and aliphatic hydrocarbons.

EXAMPLE 26

The preparative method of Example 26 is repeated except 0.1 mole of p-phenylene diamine is used in place of 0.2 mole of aniline. The residue is p-phenylene-4-[polypropylcarbophenoxy] phthalimide which is soluble in lubricating oil and aliphatic hydrocarbons.

EXAMPLE 27

A solution of 0.2 mole 4-[polybutylcarbophenoxy] phthalic anhydride wherein the polybutyl-substituent has a 960 $\overline{M}_n$ or 61 number average carbon atoms in n-hexane is prepared. This solution is stirred and heated to 140°F. and then 0.1 mole of hexamethylene diamine is added. The resulting stirred mixture is heated at n-hexane reflux temperature for 3 hours and then n-hexane is removed by distillation. The residue is hexamethylene-di-4-[polybutylcarbophenoxy] phthalimide which is soluble in lubricating oil and aliphatic hydrocarbons.

EXAMPLE 28

The preparative method of Example 27 is repeated except 0.1 mole of 1,4-cyclohexane diamine is used in place of 0.1 mole of hexamethylene diamine. The residue is di-4-[polybutylcarbophenoxy] phthalimide of 1,4-cyclohexane diamine which is soluble in lubricating oil and aliphatic hydrocarbons.

EXAMPLE 29

The solution of the 4-[polybutylcarbophenoxy] phthalic anhydride described as the product of Example 1 is converted to a solution of the corresponding phthalic acid in the following manner. To 380 grams of said solution (0.086 mole of said phthalic anhydride) heated to 150°F. there is added 100 ml. hot (150°F.) water. The resulting mixture is vigorously stirred for 8 hours and then heated to 180°F. at reduced pressure of 300 Hg. while nitrogen gas is injected into the mixture to assist removal of unreacted water. The water free solution contains 40.3 weight percent 4-[polybutyl carbophenoxy] phthalic acid wherein the polybutyl-substituent has a 1500 $\overline{M}_n$ or 107 number average carbon atoms.

The following uses in crankcase lubricant oils of some of the foregoing illustrative examples are given to illustrate the use of the present inventive compounds as detergent-dispersant addition agent for lubricating oils. Said utility can be demonstrated by a Spot Dispersancy Test in which 0.5 gram of such compound is added to a measured volume of used crankcase oil which contains sludge to the extent the original dispersant-detergent addition agent is no longer capable of keeping the sludge suspended in the oil. To do this the mixture of 0.5 gram of the detergent-dispersant addition agent candidate is thoroughly mixed with the measured amount of used test oil (crankcase oil resulting from a Lincoln Engine Sequence V Test run for 384 hours), the stirred mixture is heated to 360°F. for 16 hours. As a control for purposes of comparison, the same volume of used crankcase oil is likewise heated and stirred to 360°F. for 16 hours without the addition of any fresh addition agent. Equal aliquot portions of each of the hot oils are deposited on different marked areas of a large sheet of blotter paper. The blotter paper is held at room temperature for 24 hours. The spot deposits develop into two separate, concentric rings. The inner ring is the sludge ring and the outer ring is the sludge free oil ring. The diameters of these rings are measured and the ratio of the diameter of the sludge ring (Ds) to the diameter of the oil ring (Do) times 100 (Ds/Do × 100), an indicator of dispersancy function of the tested candidate, is calculated. Said 0.5 gram of test candidate means 0.5 gram of diacid, imide, amide or ester product of the indicated present inventive composition and not of the solution thereof prepared by the reference example. Thus all the candidates were tested on the same weight basis. The results of such tests are shown in TABLE I. Ideally Ds/Do × 100 should be 100.

TABLE I

| Candidate Added | SPOT DISPERSANCY TEST Composition Type | Ds/Do × 100 |
|---|---|---|
| Example 2 | Ester | 79 |
| Example 4 | Ester | 64 |
| Example 5 | Ester | 78 |
| Example 7 | Ester | 85 |
| Example 8 | Ester | 58 |
| Example 9 | Ester | 80 |
| Example 10 | Ester | 63 |
| Example 11 | Ester | 44* |
| Example 17 | Imide | 42* |
| Example 18 | Imide | 43* |
| Example 19 | Imide | 79 |
| Example 20 | Imide | 87 |
| Example 21 | Imide | 80 |
| Example 32 | Diacid | 51 |
| Control | — | 60 |

*Low values caused by presence of unreacted amine.

Another test is an actual test in a crankcase lubricating oil formulation use in types of gasoline powered engines of types commonly in actual commercial use. These engines tests are stand-run in contrast to run under actual use, i.e., in a passenger automobile. Three such engine tests here reported: Ford 289 cubic inch Engine Test, L-38 Engine Test and Caterpillar 1-H Engine Test are industry accepted tests conducted under conditions of operation accepted and approved by the various members of industry (oil formulators, engine manufacturers and Military Procurement Agency).

In the first two indicated engine tests the product of Example 2 (solution) was used as 5 volume percent in fresh base stock lubricating oil with anti-oxidant, anti-wear, anti-corrosion and viscosity-improver addition agents to prepare a 10w-30 lubricating oil. The Ford 289 Engine Test is severe test for sludge and Varnish deposit formation. The L-38 (also known s CLR-38) Engine Test is conducted to evaluate high temperature oxidation stability and Cu-Pb bearing corrosion. With respect to oxidation stability the oil performance is rated on a pass or fail evaluation based on oxidation by-product formation and Cu-Pb bearing loss. The Ford 289 Engine Test is sludge rated on numerical scale of 0–50 (50 is clean engine internals) and 0–50 varnish deposit on a like scale of 0–50 (again 50 is clean engine internals).

In those two tests the product (solution) of Example 2 glycerol ester product gave a 44 sludge and 42 varnish ratings in the Ford 289 Engine Test and a pass on oxidation with a 17 mg bearing weight loss from the L-38 Engine Test.

In the third Engine test (Caterpillar 1-H Engine Test) the solution product of Example 2 was used at 4 volume percent as detergent in fresh base stock lubricating oil together with anti-wear, anti-oxidant and anti-corrosion addition agents to prepare a diesel engine crankcase lubricating oil. This engine test is for high temperature detergency function of the candidate addition agent and is rated pass or fail on the bases of nature and amount of deposits in (amount filling) the four piston grooves, on (covering) the three piston lands and on (covering) the piston undercrown after 240 and 480 hours of engine operation under test conditions. The deposit evaluations are tabulated below and each test was rated "pass."

| Piston Portion | Amount and Nature of Deposits | |
|---|---|---|
| | 240 Hours | 480 Hours |
| Top Groove | 11% filled:61% carbon-39% lacquer | 18% filled:88% carbon-12% lacquer |
| 2nd Groove | clean | 4% very light lacquer |
| 3rd Groove | clean | clean |
| 4th Groove | clean | clean |
| 1st Land | 32% lacquer | 44% lacquer |
| 2nd Land | clean | clean |
| 3rd Land | clean | clean |
| Undercrown | 25% lacquer | 50% lacquer |

The compounds of Formula I, 4-(alkyl-substituted carbophenoxy) phthalic anhydride, wherein the alkyl-substituent hs 30 or more carbon atoms, and their dicarboxylic acid analogs are useful as anti-wear and anti-corrosion addition agents for lubricating oils where detergency or dispersancy is not needed or desirable for example in turbine oils as a replacement for the $C_6$–$C_{30}$ alkyl- and alkenyl-substituted succinic anhydrides and acids previously used in turbine oils as anti-wear and anti-corrosion agents. Said compounds of formula I also are useful as anti-wear and anti-corrosion agents in cutting oils and in greases. The compositions of this invention are useful in hydrocarbon mixed oils for the purposes disclosed and illustrated in concentrations of 0.1 to 50 weight percent.

Ester, amide and imide derivatives of compounds of Formula I will, from the respective illustrative esters, amides and imides, become obvious to those skilled in the art.

What is claimed is:

1. A N-4(alkylcarbophenoxy) phthalimide of the alkylene polyamine of the formula H N—(A—NH)$_n$H wherein A is divalent ethylene and $n$ is from 1–10 and wherein the alkyl-substituent contains 30–214 carbon atoms.

2. The imide of claim 1 which is tetraethylene pentamine di-4-(polybutylcarbophenoxy) phthalimide wherein the polybutyl-substituent has the $\overline{M}_n$ of 1500.

3. The N,N'-bis-aminopropyl piperazine di-4-(polybutylcarbophenoxy) phthalimide wherein the polybutyl-substituent has the $\overline{M}_n$ of 1500.

4. The N,N'-bis-aminopropyl piperazine-4-(polybutylcarbophenoxy) phthalimide wherein the polybutyl-substituent has the $\overline{M}_n$ of 1500.

5. The N,N'-dimethylethylene-diamine-4-(polybutylcarbophenoxy) phthalimide wherein the polybutyl-substituent has the $\overline{M}_n$ of 1500.

6. The N',N'-dihydroxyethyl ethylenediamine-4-(polypropylcarbophenoxy) phthalimide wherein the polypropyl-substituent has the $\overline{M}_n$ of 425.

7. The N,N'-hexamethylene-diamine-di-4-(polybutylcarbophenoxy) phthalimide wherein the polybutyl-substituent has the $\overline{M}_n$ of 960.

* * * * *

UNITED STATES PATENT OFFICE
CERTIFICATE OF CORRECTION

Patent No. 3,951,977  Dated April 20, 1976

Inventor(s) EDMUND J. PIASEK and IMRE PUSKAS

It is certified that error appears in the above-identified patent and that said Letters Patent are hereby corrected as shown below:

Under "United States Patent" [19] change "Plasek et al." to

-- Piasek et al. --.

After [75] "Inventors:" change "Edmund J. Plasek" to -- Edmund J. Piasek --.

Column 4, line 42, change "poly-alcohols" to -- poly-alkoxy alcohols --.

Column 6, line 31, change "tri-hydroyethyl" to -- tri-hydroxyethyl --.

Column 6, line 51, change "Mn" to -- $\overline{M}_n$ --.

Column 11, line 42, change "300 Hg" to -- 300 mm Hg --.

Column 12, line 51, after "known" change "s" to -- as --.

Column 13, line 25, after "substituent" change "hs" to -- has --.

Signed and Sealed this

Seventh Day of September 1976

[SEAL]

Attest:

RUTH C. MASON
*Attesting Officer*

C. MARSHALL DANN
*Commissioner of Patents and Trademarks*